US006917738B2

United States Patent
Guerra et al.

(10) Patent No.: US 6,917,738 B2
(45) Date of Patent: Jul. 12, 2005

(54) OPTICAL FIBER SYSTEM WITH SEALED FIBER BUNDLE

(75) Inventors: David J. Guerra, Putnam, CT (US); James P. Barry, Charlton, MA (US)

(73) Assignee: Karl Storz Endovision, Charlton, MA (US)

( * ) Notice: Subject to any disclaimer, the term of this patent is extended or adjusted under 35 U.S.C. 154(b) by 171 days.

(21) Appl. No.: 10/319,963

(22) Filed: Dec. 16, 2002

(65) Prior Publication Data

US 2004/0114891 A1 Jun. 17, 2004

(51) Int. Cl.$^7$ .................................................. G02B 6/06
(52) U.S. Cl. ........................................ 385/117; 385/116
(58) Field of Search ................................ 385/115, 116, 385/117

(56) References Cited

U.S. PATENT DOCUMENTS

| | | | |
|---|---|---|---|
| 3,740,115 A | * | 6/1973 | Cole .............................. 385/25 |
| 4,158,477 A | | 6/1979 | Phillips et al. |
| 4,422,715 A | | 12/1983 | Williams et al. |
| 4,641,912 A | | 2/1987 | Goldenberg |
| 4,669,818 A | | 6/1987 | Myer |
| 4,697,576 A | | 10/1987 | Krauter |
| 4,709,981 A | | 12/1987 | Mori |
| 4,807,597 A | | 2/1989 | Tsuno et al. |
| 4,900,124 A | | 2/1990 | Lampert et al. |
| 5,170,454 A | * | 12/1992 | Kanai ............................ 385/88 |
| 5,347,990 A | | 9/1994 | Ebling et al. |
| 5,377,668 A | | 1/1995 | Ehmsen et al. |
| 5,452,395 A | | 9/1995 | Schichman et al. |
| 5,569,161 A | | 10/1996 | Ebling et al. |
| 5,665,051 A | | 9/1997 | Quick et al. |
| 6,063,024 A | | 5/2000 | Yamamoto |
| 6,254,282 B1 | | 7/2001 | Ishihara et al. |
| 6,293,910 B1 | | 9/2001 | Yamakita et al. |
| 6,356,700 B1 | | 3/2002 | Strobl |

* cited by examiner

Primary Examiner—John D. Lee
Assistant Examiner—Jennifer Doan
(74) Attorney, Agent, or Firm—St. Onge Steward Johnston & Reens LLC

(57) ABSTRACT

An optical fiber imaging system includes an optical fiber bundle including a plurality of optical fibers, an elongated housing receiving and at least partially enclosing the optical fiber bundle therein, and an optical window disposed at an end of the elongated housing and thereby defining a cavity within the elongated housing next to the end face of the fiber bundle, the cavity being adapted to retain a substance of inert chemistry such as index matched oil for suppressing environmental degradation at the end face of the fiber bundle. The oil is preferably made of silicone petroleum products with the index of refraction being advantageous to the preferred optical characteristics of the entire imaging system.

11 Claims, 1 Drawing Sheet

OPTICAL FIBER SYSTEM WITH SEALED FIBER BUNDLE

FIELD OF THE INVENTION

The present invention relates generally to a fiber optics imaging system and more particularly to an optical fiber imaging system having a fiber bundle with its ends sealed with inert media.

BACKGROUND OF THE INVENTION

The use of endoscopes for diagnostic and therapeutic purposes is well known in the medical field. Conventional flexible endoscopes incorporate a bundle of thin and flexible optical fibers for transmitting images or light illumination from and/or to an object distal to the insertion section of the endoscope. The fiber optic bundle typically comprises a plurality of optical fibers of glass or optical plastic.

Known problems associated with the use of fiber optic bundles include their degradation when used over a period of time. Such degradation is in part due to the repetitive flexing of the bundles during maneuvering about the operative site in the course of surgical procedures. It is also well known in the art that typical environmental degradation of fiber bundles includes development of harmful cracks occurring particularly at the imaging end faces of the bundles.

The fiber optic bundles are often joined with other optical components such as lenses, apertures and prisms, etc. The interface between these components is typically made of transparent adhesives applied there-between or, in the absence of adhesive, by maintaining an air gap at the interface. However, since the fiber optic end faces are very susceptible to environmental degradation, they may be deteriorated in the presence of air, moisture, or pH unbalanced adhesives at the interface.

SUMMARY OF THE INVENTION

Accordingly, the present invention is directed to an optical fiber imaging system, and in particular to an optical fiber imaging system having a fiber bundle with its ends sealed with inert media. The optical fiber imaging system of the invention generally contemplates the replacement of the interface media (e.g., adhesives or air gap) between the fiber bundle and associated optical components with a substance of relatively inert chemistry capable of suppressing environmental degradation of the fiber bundle. The substance preferably has an index of refraction which generally matches that of the optical fibers or other associated optical components therein.

In accordance with one preferred embodiment of the invention, the optical fiber imaging system includes a fiber bundle formed from a plurality of optical fibers, an elongated housing receiving and at least partially enclosing the optical fiber bundle therein, and a window disposed at an end of the elongated housing and thereby defining a cavity within the elongated housing next to an end of the fiber bundle, and a substance of inert chemistry filled therein the cavity for suppressing environmental degradation at the end face of the fiber bundle. The substance is preferably oil made of silicone or petroleum products with the index of refraction chosen to be advantageous to the preferred optical characteristics of the entire imaging system. In the preferred embodiment, the oil is entrapped in the cavity having a capsule-like space created by the components surrounding the distal and/or proximal end of the fiber bundle. The optical fiber imaging system of the invention preferably includes a seal disposed about the optical window and the fiber bundle for preventing leakage of the index matched oil from the cavity.

BRIEF DESCRIPTION OF THE DRAWINGS

A preferred embodiment of the invention is described herein with reference to the drawings, wherein.

DETAILED DESCRIPTION OF PREFERRED EMBODIMENTS

Figure 1:
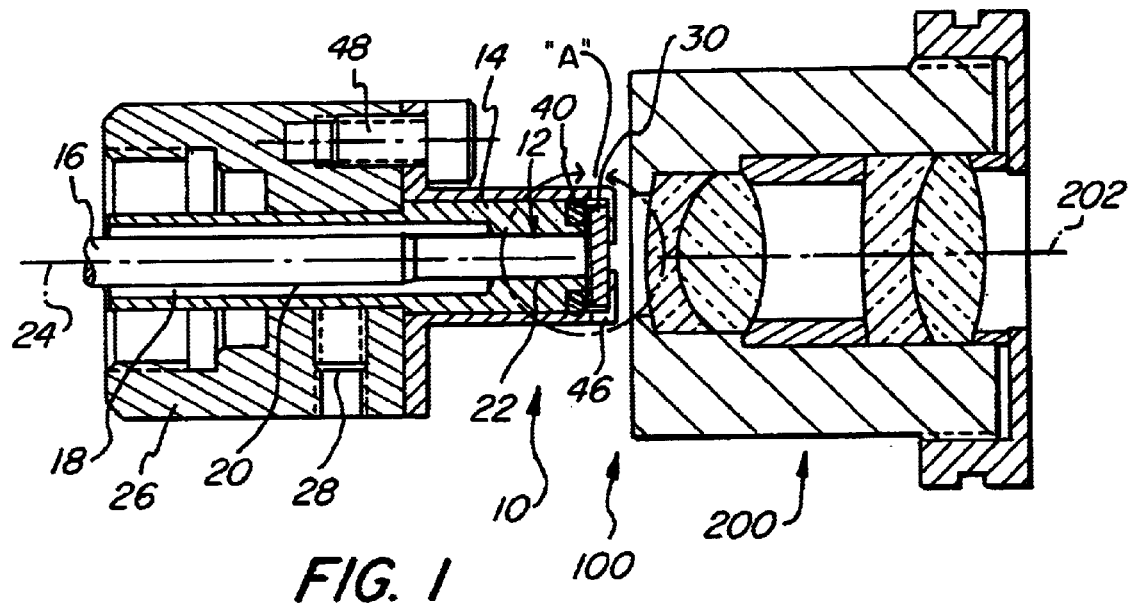
FIG. 1 is a cross-sectional view of the optical fiber imaging system constructed in accordance with the principles of the present invention along with a conventional optical system of an endoscope.
Figure 2:
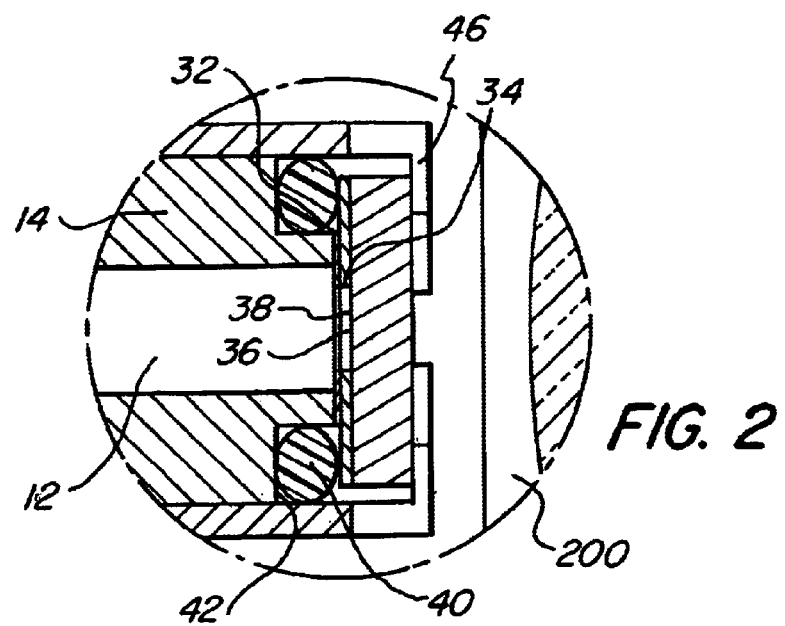
FIG. 2 is an enlarged cross-sectional view of the optical fiber imaging system of FIG. 1, illustrating the details of section "A" in FIG. 1.

Referring now to the drawings, FIGS. 1 and 2 illustrate the optical fiber imaging system constructed in accordance with the principles of the present invention. The invention is described herein in connection with an endoscopic apparatus, however, the optical fiber imaging system of the invention is also useful for other products including, without limitation to, any communication or electronics devices utilizing optical fibers therein.

FIG. 1 illustrate optical fiber imaging system 10 of the invention constructed as a component of, for example, an endoscope 100 including a conventional optical system such as lens assembly 200. Optical fiber imaging system 10 includes optical fiber bundle 12 and elongated hollow housing 14 receiving and at least partially enclosing the fiber bundle 12 therein. Fiber bundle 12 includes a plurality of optical fibers 16 for transmitting light or images therethrough. Elongated housing 14 defines central bore 18 for receiving the fiber bundle 12 therein. Central bore 18 preferably includes wide portion 20 and narrow portion 22, wherein the narrow portion is configured to tightly receive therein an end portion of the fiber bundle 12 and defining a longitudinal axis 24 in alignment with longitudinal axis 202 of the associated optical system, for example, lens assembly 200. Distal face portion of elongated housing 14 is preferably flush with the distal face of fiber bundle 12 as shown in FIG. 2. Optical fiber imaging system 10 preferable includes outer casing 26 around a periphery of housing 14, which is fixed thereto by set screw 28.

Optical fiber imaging system 10 further includes optical window or cover 30 made of optically clear material. Optical window 30 includes distal and proximal flat end faces and has a refractive index similar to the refractive index of the optical fibers 16. Thin flat spacer 32 with central bore 34 is preferably provided between the distal end face of housing 14 and optical window 30 in a water tight manner. The central bore 34 of spacer 32 defines a cavity 36 when the components are assembled. Cavity 36 is for receiving an inert substance such as index matched oil 38 of relatively inert chemistry therein. The oil is to be particularly chosen to include the characteristics inert or carrying a minimal impact to the surrounding optical components, preferably with a refractive index advantageous to the entire optical imaging system. Preferred examples of such oil include those made of silicone or petroleum products with a refractive index selected to be similar to that of optical fibers 16 and optical window 30. Any other suitable fluid of relatively inert chemistry may be also used. For further restricting leakage of the index matched oil, seal members such as O-ring 40 is positioned about the optical window 30 preferably within groove portion 42 disposed at a distal end face of elongated housing 14. Clamping member 46 is provided to tightly hold optical window 30 and spacer 32 in position. Bolt 48 is provided to attach clamping member 46 to casing 26. Other conventional clamping means known in the art may be utilized to hold the components in position.

Conceivable advantages of the present invention utilizing the liquid interface masking system as exemplified hereinabove include, without limitation to:

a. It eliminates environmental degradation, particularly at the end faces, of the optical fiber bundle;

b. It eases manufacture and omits the cumbersome use of adhesives or air gap spacers at the interface;

c. A better optical performance is achievable by using index matched oil at the interface;

d. The index matched oil and/or the optical window are easily replaceable (or refillable) by appropriate ones;

e. It eliminates the need for optical coatings on the fiber optics for suppressing the degradation thereof; and f. It improves light transmission by acting as an AR surface.

Although the invention has been described and illustrated with respect to the exemplary embodiment thereof, it should be understood by those skilled in the art that various other changes, omissions, and additions may be made therein and thereto, without parting from the spirit and scope of the present invention.

What is claimed is:

1. An optical fiber imaging system for endoscopy comprising:

a fiber bundle formed from a plurality of optical fibers and having a generally flat end face;

an elongated housing receiving and at least partially enclosing said fiber bundle therein;

a window disposed at an end of said elongated housing and thereby defining a cavity within said elongated housing next to the end face of said fiber bundle; and a substance of inert chemistry filling the cavity, said substance having a refractive index between the refractive indices of the optical fibers and the window, said substance having a property capable of suppressing environmental degradation in the end face of said fiber bundle occurring from extended use of the optical fiber imaging system.

2. The optical fiber imaging system of claim 1, wherein said substance of inert chemistry is fluid.

3. The optical fiber imaging system of claim 2, wherein said substance has a refractive index advantageous to the optical characteristics of the optical fiber imaging system.

4. The optical fiber imaging system of claim 3, wherein said substance has a refractive index generally the same as the refractive index of the window.

5. The optical fiber imaging system of claim 2, wherein said substance is oil.

6. The optical fiber imaging system of claim 5, wherein the oil is made of silicone or petroleum products.

7. The optical fiber imaging system of claim 1 further including a seal disposed about said window for restricting leakage of the substance from the cavity.

8. The optical fiber imaging system of claim 7, wherein said seal includes an O-ring disposed around the outer periphery of said window.

9. The optical fiber imaging system of claim 7 further including a spacer positioned between said window and said elongated housing.

10. An endoscope comprising:

a plurality of optical fibers;

a fiber bundle formed from said plurality of optical fibers and having a generally flat end face;

an elongated housing receiving said fiber bundle therein;

a cover disposed at an end of said elongated housing and thereby defining a cavity within said elongated housing adjacent the end face of said fiber bundle; and a substance of inert chemistry filling the cavity, said substance having a refractive index between the refractive indices of the optical fibers and the window, said substance having a property capable of suppressing environmental degradation in the end face of said fiber bundle occurring from extended use of the optical fiber imaging system.

11. The endoscope of claim 10, wherein said substance has a refractive index advantageous to the optical characteristics of the endoscope.

* * * * *